United States Patent
Govari et al.

(10) Patent No.: US 10,342,572 B2
(45) Date of Patent: Jul. 9, 2019

(54) GEAR MECHANISM TO DRIVE OSCILLATING SHAFT

(71) Applicant: Biosense Webster (Israel) Ltd., Yokneam (IL)

(72) Inventors: Assaf Govari, Haifa (IL); Yehuda Algawi, Binyamina (IL); Ilan Grunberg, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 170 days.

(21) Appl. No.: 15/236,905

(22) Filed: Aug. 15, 2016

(65) Prior Publication Data

US 2018/0042641 A1    Feb. 15, 2018

(51) Int. Cl.
*A61B 17/32* (2006.01)
*A61B 17/3207* (2006.01)
*F16H 19/08* (2006.01)
*A61F 9/007* (2006.01)
*A61B 17/00* (2006.01)

(52) U.S. Cl.
CPC ............... *A61B 17/320758* (2013.01); *A61B 17/32002* (2013.01); *A61B 17/320783* (2013.01); *A61F 9/00763* (2013.01); *F16H 19/08* (2013.01); *A61B 2017/00424* (2013.01); *A61B 2017/320028* (2013.01); *A61B 2017/320064* (2013.01)

(58) Field of Classification Search
CPC . A61B 17/3207; A61B 17/3205; A61B 17/24; A61B 17/32; A61B 17/32002; A61B 17/320758; A61B 2017/320064; A61B 2017/320028; A61B 2017/00261; A61B 17/320783; A61F 9/00763
See application file for complete search history.

(56) References Cited

U.S. PATENT DOCUMENTS

| | | | |
|---|---|---|---|
| 5,591,170 A | 1/1997 | Spievack et al. | |
| 5,769,086 A | 6/1998 | Ritchart et al. | |
| 8,298,254 B2 | 10/2012 | Dubois et al. | |
| 2010/0063415 A1 | 3/2010 | Richart et al. | |
| 2010/0125287 A1 | 5/2010 | Cole et al. | |
| 2012/0004595 A1 | 1/2012 | Dubois et al. | |
| 2012/0172889 A1* | 7/2012 | Chin | A61B 17/32002 606/119 |
| 2014/0100567 A1 | 4/2014 | Edwards et al. | |

OTHER PUBLICATIONS

European Search Report and Written Opinion dated Jan. 3, 2018 for Application No. 17186109.9, 5 pages.

* cited by examiner

*Primary Examiner* — Vi X Nguyen
(74) *Attorney, Agent, or Firm* — Frost Brown Todd LLC

(57) ABSTRACT

A cutting operation is performed with an apparatus having an elongated sleeve with a port in its distal section. The sleeve is connected to a vacuum source and a rotating shaft is disposed in the lumen of the sleeve. The shaft has a cutting blade at its distal end opposite the port. The blade has two cutting edges, a gear assembly operative to alternately rotate the shaft in a first direction and a second direction about the axis of symmetry of the shaft, and a motor for powering the gear assembly.

20 Claims, 4 Drawing Sheets

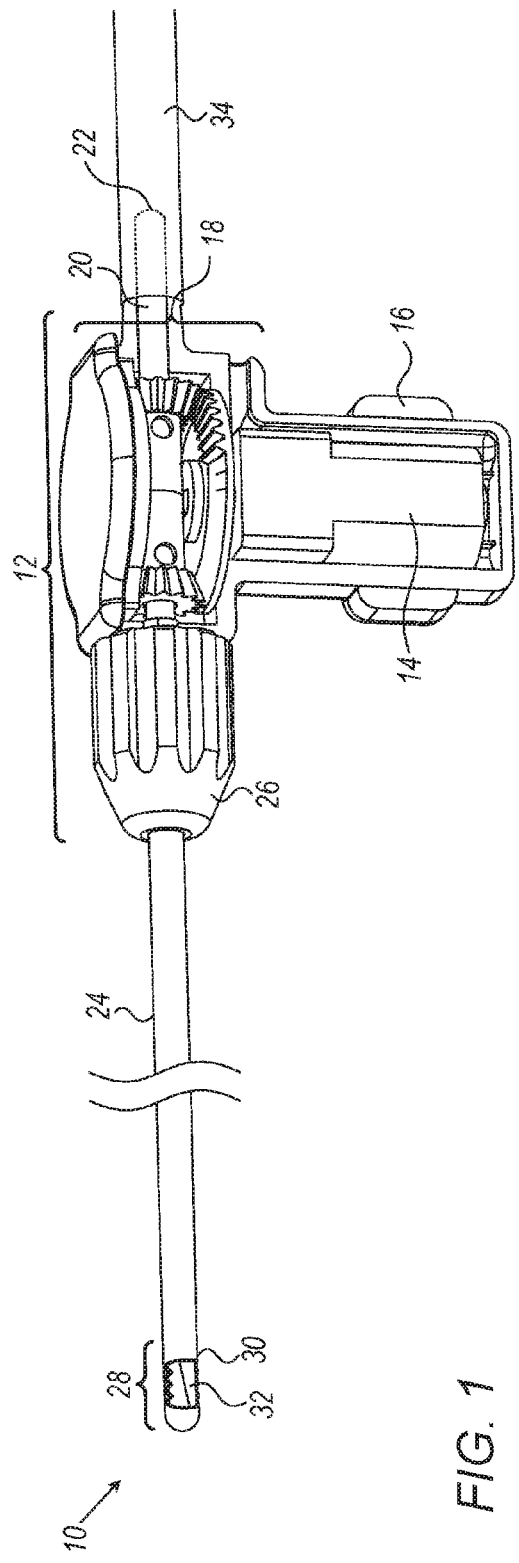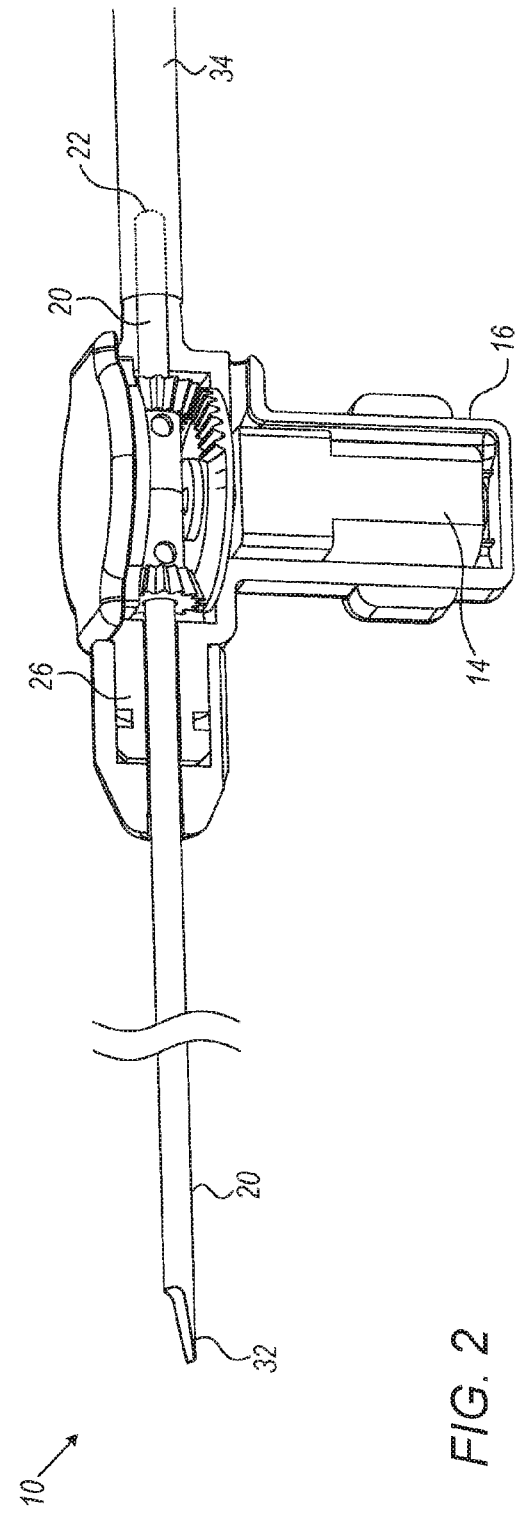
FIG. 1
FIG. 2

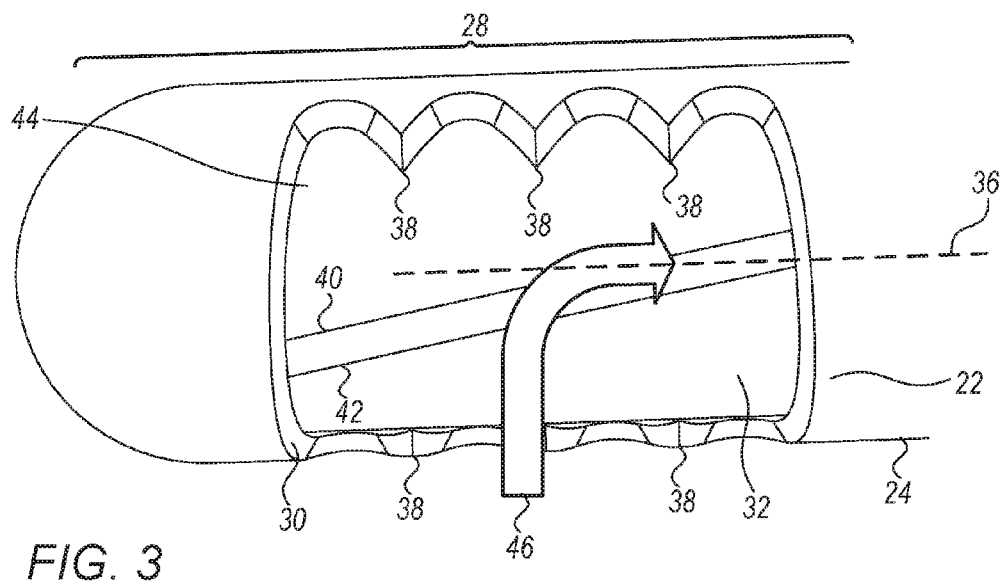
FIG. 3
FIG. 4
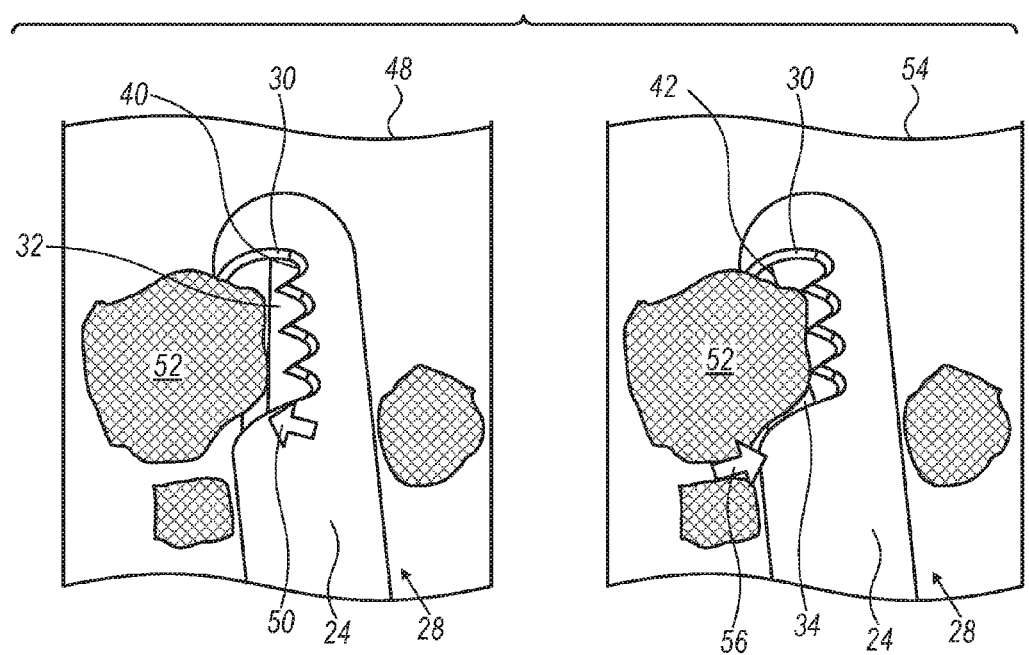

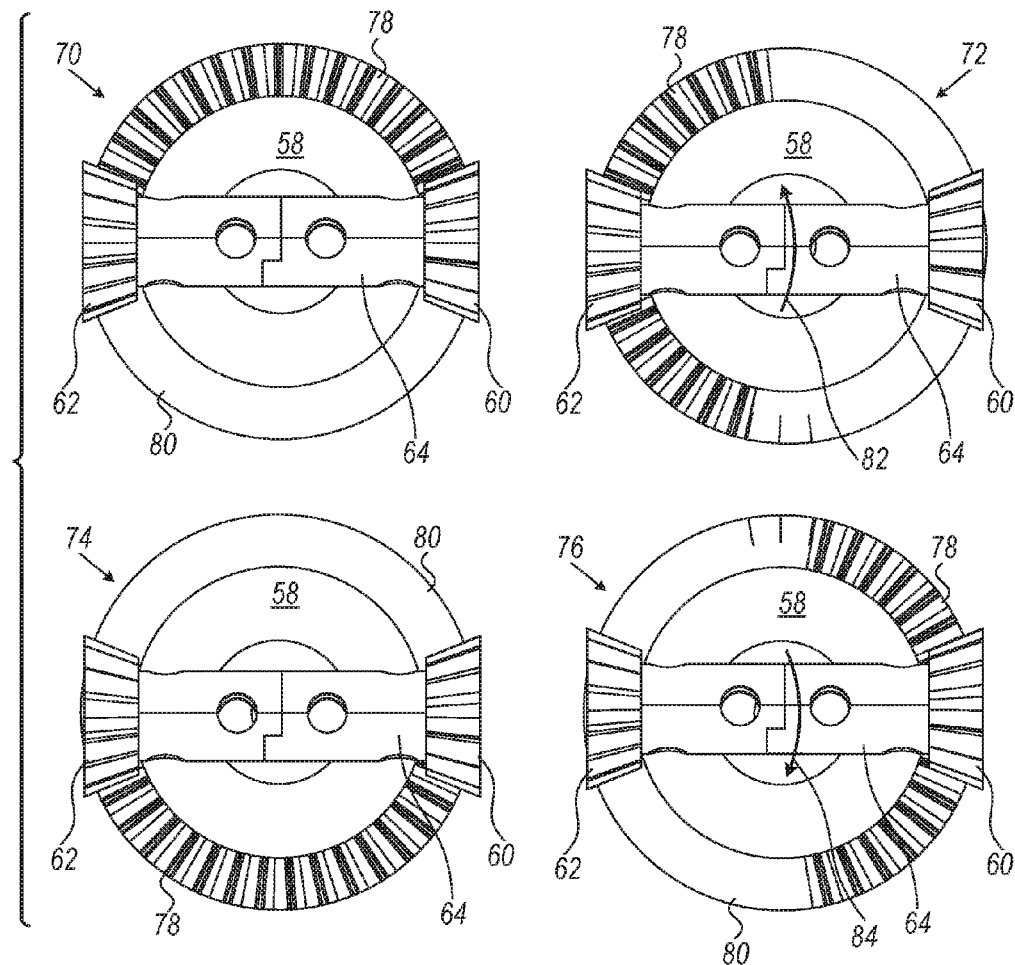
FIG. 6
FIG. 7
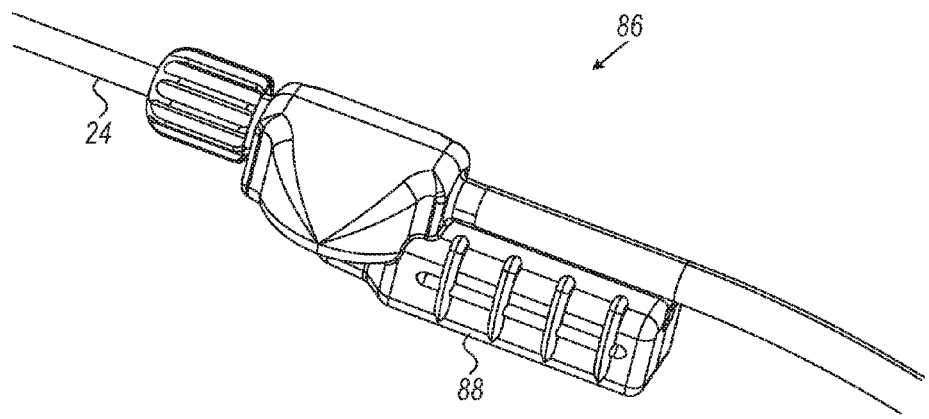

GEAR MECHANISM TO DRIVE OSCILLATING SHAFT

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments for removal of tissue. More particularly, this invention relates to a cutting device adapted for the sinus or nose.

2. Description of the Related Art

Powered devices for performing debridement and polypectomy in hollow spaces, such as the paranasal sinuses have been the subject of considerable efforts. The devices must be capable of navigating narrow, sometimes tortuous channels to reach the objects of such medical procedures without damage to delicate structures in the body—and yet be sufficiently light and convenient to manipulate in order that the operator can endure protracted operations.

An example of such devices is proposed in U.S. Pat. No. 8,298,254, which proposes a polypectomy device utilizing a reciprocating mechanism or motor powered by suction from a vacuum source.

In another example, U.S. Patent Application Publication No. 2010/0063415, issued as U.S. Pat. No. 7,918,803 on Apr. 5, 2011, discloses a biopsy device that includes a needle having a lateral opening for receiving tissue. The needle may be rotatable with respect to a portion of the biopsy device, such as a housing of the biopsy device, and the needle may be offset from a center of the housing. A hollow cutter is employed for cutting tissue received in the lateral opening of the needle.

SUMMARY OF THE INVENTION

In medical procedures where tissue is removed, such as sinuplasty procedures, it is advantageous that the cutter performing the removal be oscillatory Embodiments of the present invention provide an oscillating gear assembly to drive an oscillating cutter for use in a catheter for removal of tissue or polyps.

There is provided according to embodiments of the invention a cutting apparatus having an elongated sleeve with a port in its distal section. The sleeve is connected to a vacuum source and a rotating shaft is disposed in the lumen of the sleeve. The shaft has a cutting blade at its distal end opposite the port. The blade has two cutting edges, a gear assembly operative to alternately rotate the shaft in a first direction and a second direction about the axis of symmetry of the shaft, and a motor for powering the gear assembly.

According to an aspect of the apparatus, the port has two sides and a series of teeth formed on the two sides.

According to an additional aspect of the apparatus, the blade is inclined outwardly and distally toward the inner wall of the sleeve.

According to another aspect of the apparatus, the gear assembly includes a drive gear rotated by the motor. The drive gear has a toothed portion and two driven gears mounted on a common shaft that is coupled to the sleeve, the driven gears alternately engaging the toothed portion.

One aspect of the apparatus includes a housing for the motor, wherein the housing is configured as a grip.

According to yet another aspect of the apparatus, a length dimension of the housing is oriented perpendicular to the sleeve.

According to still another aspect of the apparatus, a length dimension of the housing is oriented perpendicular to the sleeve.

According to a further aspect of the apparatus, the motor is an electric motor that may be powered by direct current.

There is further provided according to embodiments of the invention a method, which is carried out by inserting a cutting device into a body of a living subject adjacent a target tissue to be resected, actuating the cutting device to resect the target tissue. The cutting device is formed as an elongated sleeve having a port in its distal section connected to a vacuum source and a rotating shaft in the lumen of the sleeve. The shaft has a cutting blade disposed at its distal end opposite the port. The blade has two cutting edges, a gear assembly operative to alternately rotate the shaft in a first direction and a second direction about the axis of symmetry of the shaft, and a motor for powering the gear assembly.

According to an additional aspect of the method, the gear assembly includes a drive gear rotated by the motor. The drive gear has a toothed portion and two driven gears mounted on a common shaft that is coupled to the sleeve, the driven gears alternately engaging the toothed portion.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 1 is a perspective view of a tissue removal device in accordance with an embodiment of the invention;

FIG. 2 is a perspective, partially cutaway view of the tissue removal device shown in FIG. 1 in accordance with an embodiment of the invention;

FIG. 3 is an elevation of the distal section of the tissue removal device shown in FIG. 1 in accordance with an embodiment of the invention;

FIG. 4 is a sequence of two views of the distal section of the tissue removal device shown in FIG. 1 in accordance with an embodiment of the invention;

FIG. 6 is a series of four phases of the operation of a portion of the gear assembly shown in FIG. 1 in accordance with an embodiment of the invention; and FIG. 7 is an elevation of a tissue removal device in accordance with an alternate embodiment of the invention.

DETAILED DESCRIPTION OF THE INVENTION

Figure 5:
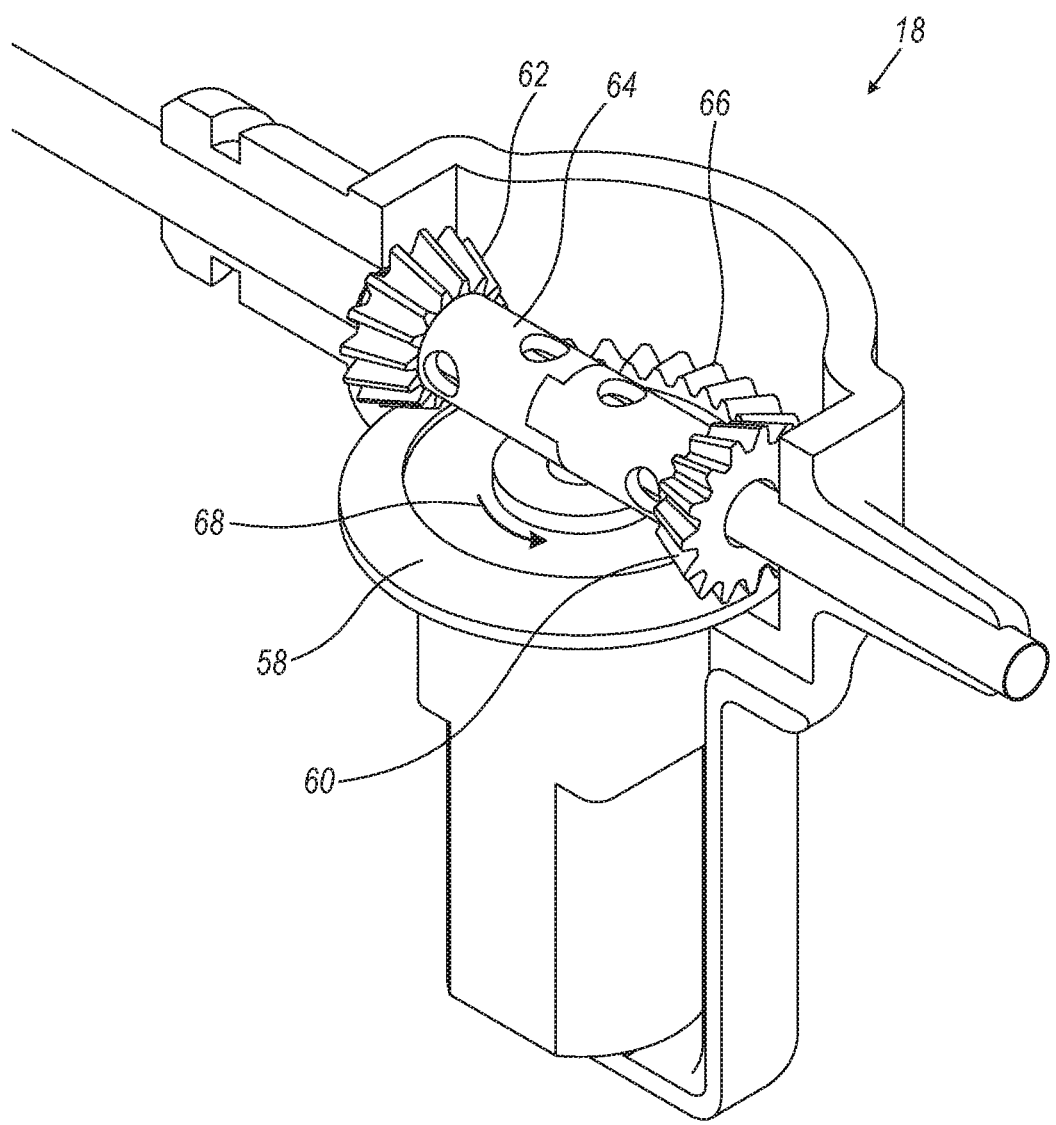
FIG. 5 is a cutaway top view in slight perspective of the gear assembly of the tissue removal device shown in FIG. 1 in accordance with an embodiment of the invention.

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", "links", "couple" and "couples" are intended to mean either an indirect or direct connection. Thus, if a first device couples to a second device, that connection may be through a direct connection, or through an indirect connection via other devices and connections.

Turning now to the drawings, reference is initially made to FIG. 1, which is a perspective view of a tissue removal device 10 in accordance with an embodiment of the invention. The tissue removal device 10 has a drive section 12 including a motor 14. The drive section 12 is enclosed in a housing 16, which protects the motor 14. The housing 16 is oriented perpendicular to an elongated sleeve 24 and functions as a hand grip for the operator. The housing 16 is partially removed in FIG. 1 for clarity of presentation. The motor 14 may be an electric motor, driven by direct current, such as produced by a battery (not shown). Other types of power may operate the motor 14, for example alternating current, hydraulics, or vacuum.

The drive section 12 includes an oscillatory gear assembly 18 linked to the motor 14. The gear assembly 18 is arranged to impart a reciprocating rotatory motion to a cylindrical shaft 20 having a lumen 22. The shaft 20 extends through the sleeve 24. Stability for the sleeve 24 is provided by a sleeve adapter 26, which extends distally from the housing 16.

The tissue removal device 10 has a distal section 28, wherein the sleeve 24 is provided with a port 30 that exposes a cutting blade 32. The blade 32 forms an extension of the distal portion of the shaft 20. A vacuum hose 34 connected to a vacuum pump (not shown) and to the proximal end of the tissue removal device 10 provides vacuum to the port 30 via the sleeve 24 or the lumen 22 of the shaft 20. The terms "proximal" and "distal" are used arbitrarily herein to distinguish the two ends of the tissue removal device 10. These terms have no physical meanings with respect to the actual configuration of the tissue removal device 10.

Reference is now made to FIG. 2, which is a perspective, partially cutaway view of the tissue removal device 10 in accordance with an embodiment of the invention. The sleeve 24 (FIG. 1) and a portion of the sleeve adapter 26 are omitted. The blade 32 is a distal extension of the shaft 20.

Reference is now made to FIG. 3, which is an elevation of the distal section 28 of the sleeve 24, in accordance with an embodiment of the invention. The port 30 is approximately rectangular, with its length dimension paralleling an axis of symmetry 36 that is common to the shaft 20 (FIG. 2) and the sleeve 24. The sides of the port 30 are provided with a series of teeth 38, which help to stabilize the port 30 against tissue being treated when cutting force is applied by the blade 32. The blade 32 is provided with two cutting edges 40, 42 that alternate in cutting the tissue as the shaft reciprocates. Inclination of the blade 32 outwardly and distally toward inner wall 44 of the sleeve 24 as shown in FIG. 3 urges resected tissue into the lumen 22 and thence through the lumen 22 of the sleeve 24, aided by suction produced by the vacuum pump (not shown). The movement of the tissue is represented by arrow 46.

Reference is now made to FIG. 4, which is a sequence of two views of the distal section 28 illustrating the oscillatory rotation of the blade 32 in accordance with an embodiment of the invention. In diagram 48 at the left of the figure, blade 32 is rotating in the direction indicated by arrow 50 and is cutting a polyp 52 in a direction generally from its top surface toward its base. In diagram 54 the blade 32 is rotating in the opposite direction, indicated by arrow 56, and is resecting the polyp 52 in a sweeping cut generally from its base toward its top surface.

Reference is now made to FIG. 5, which is a cutaway top view of the gear assembly 18 in slight perspective in accordance with an embodiment of the invention. The gear assembly 18 comprises a bevel drive gear 58, rotated by the motor 14 (FIG. 1). The gear assembly 18 also has two driven bevel gears 60, 62 fixedly mounted on a common cutter shaft 64, which engage or disengage with the drive gear 58 as explained below.

The drive gear 58 is circular, but has teeth 66, which are formed on less than half of the perimeter of the gear. The remainder of the perimeter of the driving bevel gear has no teeth, and is planar. The drive gear 58 rotates in a single direction, for example, the direction indicated by arrow 68.

Reference is now made to FIG. 6, which is a series of four phases 70, 72, 74, 76 of the operation of a portion of the gear assembly 18 (FIG. 1) showing relationships between the drive gear 58 and the gears 60, 62 in accordance with an embodiment of the invention. As best seen in phases 72, 76, drive gear 58 has a serrated or toothed portion 78 and a planar portion 80. It will be recalled that the toothed portion 78 constitutes less than half of the circumference of the drive gear 58, so that the gear teeth of the drive gear 58 engage no more than one of the gears 60, 62 at any phase of its rotation.

In operation, one complete rotation of the drive gear 58 causes the gear assembly 18 to cycle through four stages in sequence:

In phase 70 both gears 60, a62 are disengaged from the drive gear 58. Consequently the shaft 64 (FIG. 5) is stationary.

In phase 72 the drive gear 58 has rotated 90° counterclockwise. Gear 62 engages the gear teeth of the drive gear 58, causing the shaft 64 to rotate in a first direction, as indicated by arrow 82. Gear 60 does not engage the gear teeth of the drive gear 58.

In phase 74, the drive gear 58 has rotated another 90° counterclockwise. Both gears 60, 62 are again disengaged from the drive gear 58. Consequently the shaft 64 (FIG. 5) is stationary.

In phase 76 the drive gear 58 has rotated yet another 90° counterclockwise. Gear 60 engages the gear teeth of the drive gear 58, causing the shaft 64 to rotate in a second direction, as indicated by arrow 84. Gear 62 does not engage the gear teeth of the drive gear 58.

In summary, the shaft 64 alternately rotates in the first and second directions as one and then the other of the gears 60, 62 alternately engages the gear teeth of the drive gear 58. When neither of the gears 60, 62 engages the gear teeth of the drive gear 58, the shaft 64 is stationary.

Alternate Embodiment

Reference is now made to FIG. 7, which is an elevation of a tissue removal device 86 in accordance with an alternate embodiment of the invention. The construction of the tissue removal device 86 is similar to that of the tissue removal device 10 (FIG. 1), except now a housing 88 for the motor (not shown) is oriented parallel to the sleeve 24. The housing 88 is adapted for gripping by the hand of an operator, but in some applications is particularly convenient because of the compactness of the overall design and facility of rotation by the operator about the axis of symmetry 36 (FIG. 3).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
   (a) an elongated sleeve comprising a distal section, a lumen, an inner wall and a port in the distal section, wherein the port is fluidly linked to a vacuum source;
   (b) a rotating shaft positioned in the lumen of the sleeve, wherein the shaft defines an axis of symmetry, wherein the shaft comprises a distal end and a proximal end;
   (c) a cutting blade disposed at the distal end of the shaft opposite the port;
   (d) a gear assembly operative to alternately rotate the shaft in a first direction and a second direction about the axis of symmetry; and
   (e) a motor configured to power the gear assembly, wherein the motor is configured to provide an input rotation to the gear assembly in a first angular direction, wherein the gear assembly is configured to provide the alternating rotation of the shaft in the first direction and in the second direction in response to only the input rotation in the first angular direction.

2. The apparatus according to claim 1, wherein the port comprises two sides, wherein a series of teeth are formed on the two sides.

3. The apparatus according to claim 1, wherein the blade is inclined outwardly and distally toward the inner wall of the sleeve.

4. The apparatus according to claim 1, wherein the gear assembly comprises:
   (i) a drive gear rotated by the motor, wherein the drive gear comprises a toothed portion, and
   (ii) two driven gears mounted on a common shaft coupled to the sleeve, wherein the driven gears are configured to alternately engage the toothed portion.

5. The apparatus according to claim 4, wherein the toothed portion is formed on less than half of a circumference of the drive gear.

6. The apparatus according to claim 4, wherein the drive gear rotates in a single direction to alternately rotate the shaft in the first direction and the second direction about the axis of symmetry.

7. The apparatus according to claim 1, further comprising a housing for the motor, the housing configured as a grip.

8. The apparatus according to claim 7, wherein a length dimension of the housing is oriented perpendicular to the sleeve.

9. The apparatus according to claim 1, wherein the motor is an electric motor.

10. The apparatus according to claim 1, wherein the motor is an electric motor powered by direct current.

11. The apparatus according to claim 1, wherein a length dimension of the housing is oriented parallel to the sleeve.

12. The apparatus according to claim 1, wherein the rotating shaft further comprises a lumen.

13. The apparatus according to claim 1, wherein the blade comprises two cutting edges.

14. An apparatus, comprising:
   (a) an elongated sleeve having a distal section, a lumen, an inner wall and a port in the distal section, the port linked to a vacuum source;
   (b) a rotating shaft in the lumen of the sleeve, the shaft having an axis of symmetry, a distal end and a proximal end;
   (c) a cutting blade disposed at the distal end of the shaft opposite the port, the blade having two cutting edges;
   (d) a gear assembly operative to alternately rotate the shaft in a first direction and a second direction about the axis of symmetry, wherein the gear assembly comprises:
      (i) a drive gear rotated by the motor, the drive gear having a toothed portion, and
      (ii) two driven gears mounted on a common shaft that is coupled to the sleeve, the driven gears configured to alternately engage the toothed portion; and
   (e) a motor for powering the gear assembly.

15. The apparatus according to claim 14, wherein the blade is inclined outwardly and distally toward the inner wall of the sleeve.

16. The apparatus according to claim 14, wherein the toothed portion is formed on less than half of a circumference of the drive gear.

17. The apparatus according to claim 14, wherein the drive gear rotates in a single direction to alternately rotate the shaft in the first direction and the second direction about the axis of symmetry.

18. The apparatus according to claim 14, wherein the rotating shaft further comprises a lumen.

19. The apparatus according to claim 14, wherein the blade comprises two cutting edges.

20. An apparatus, comprising:
   (a) an elongated sleeve comprising a distal end and a port through the distal end of the sleeve;
   (b) a shaft positioned in the sleeve, wherein the shaft defines a longitudinal axis, wherein the shaft comprises a distal end, wherein the shaft comprises a lumen, wherein the port is fluidly linked to a vacuum source through the shaft lumen;
   (c) a blade disposed at the distal end of the shaft;
   (d) a gear assembly configured to provide oscillatory rotation to the shaft about the longitudinal axis, wherein the gear assembly comprises:
      (i) a first gear,
      (ii) a second gear, wherein the first gear is configured to rotate the second gear as the first gear rotates through a first range of angular motion to thereby rotate the shaft in a first shaft direction, and
      (iii) a third gear, wherein the first gear is configured to rotate the third gear as the first gear rotates through a second range of angular motion to thereby rotate the shaft in a second shaft direction,
      wherein the first gear is configured to not rotate the third gear as the first gear rotates through the first range of angular motion,
      wherein the first gear is configured to not rotate the second gear as the first gear rotates through the second range of angular motion; and
   (e) a motor configured to drive the first gear.

* * * * *